US012697255B2

(12) United States Patent
Buan et al.

(10) Patent No.: US 12,697,255 B2
(45) Date of Patent: Aug. 4, 2026

(54) NEGATIVE PRESSURE DRESSING ASSEMBLY

(71) Applicant: Aatru Medical, LLC, Cleveland, OH (US)

(72) Inventors: John Buan, Maple Grove, MN (US); Richard L. Middaugh, Rocky River, OH (US); Timothy Wojciechowski, Westlake, OH (US); Thomas E. Lash, Chardon, OH (US); Edward Armstrong, Chagrin Falls, OH (US)

(73) Assignee: Aatru Medical, LLC, Cleveland, OH (US)

( * ) Notice: Subject to any disclaimer, the term of this patent is extended or adjusted under 35 U.S.C. 154(b) by 11 days.

(21) Appl. No.: 18/713,434

(22) PCT Filed: Dec. 2, 2022

(86) PCT No.: PCT/US2022/051655
§ 371 (c)(1),
(2) Date: May 24, 2024

(87) PCT Pub. No.: WO2023/107344
PCT Pub. Date: Jun. 15, 2023

(65) Prior Publication Data
US 2025/0032321 A1 Jan. 30, 2025

Related U.S. Application Data

(60) Provisional application No. 63/286,140, filed on Dec. 6, 2021.

(51) Int. Cl.
*A61F 13/00* (2024.01)
*A61F 13/05* (2024.01)
*A61M 1/00* (2006.01)

(52) U.S. Cl.
CPC .............. *A61F 13/05* (2024.01); *A61M 1/91* (2021.05); *A61M 1/962* (2021.05)

(58) Field of Classification Search
None
See application file for complete search history.

(56) References Cited

U.S. PATENT DOCUMENTS

| | | | | |
|---|---|---|---|---|
| 4,461,643 A | * | 7/1984 | Kaufman | ................. C08K 3/34 |
| | | | | 524/440 |
| 2019/0091382 A1 | * | 3/2019 | Middaugh | ............. A61M 1/964 |

(Continued)

FOREIGN PATENT DOCUMENTS

| | | |
|---|---|---|
| WO | 2018187394 A1 | 10/2018 |
| WO | 2021011181 A1 | 1/2021 |
| WO | 2023102186 A1 | 6/2023 |

OTHER PUBLICATIONS

Written Opinion of the International Searching Authority, for PCT/US/2022/051655, dated Apr. 6, 2023, 8 pages.

(Continued)

*Primary Examiner* — Kim M Lewis
(74) *Attorney, Agent, or Firm* — RANKIN, HILL & CLARK LLP

(57) ABSTRACT

A negative pressure dressing assembly includes a drape including an aperture, a cover assembly selectively sealing the aperture in an air-tight manner, a reactor configured to react with a selected gas, and a sealing liner that forms a breakable seal that prevents the reactor from being exposed to the selected gas. The drape is applied to skin to form an enclosed volume between the drape and the skin. The reactor is configured to be activated by breaking the seal, and to be put into fluid communication with the enclosed volume to consume the selected gas from the enclosed volume to create a negative pressure in the enclosed volume.

19 Claims, 8 Drawing Sheets

(56) References Cited

U.S. PATENT DOCUMENTS

| 2019/0269835 A1 | 9/2019 | Pinto et al. |
| 2019/0388278 A1 | 12/2019 | Donda et al. |
| 2021/0236701 A1 | 8/2021 | Buan et al. |

OTHER PUBLICATIONS

International Search Report, for PCT/US2022/051655, dated Apr. 6, 2023, 3 pages.
Supplementary EP Search Report filed in EP22904945 dated Sep. 3, 2025.

\* cited by examiner

NEGATIVE PRESSURE DRESSING ASSEMBLY

CROSS REFERENCE TO RELATED APPLICATIONS

This application claims the benefit of U.S. Provisional Patent Application Ser. No. 63/286,140 filed Dec. 6, 2021, which is incorporated herein by reference.

BACKGROUND

Negative pressure therapy is a treatment that utilizes negative pressure for skin treatments and restorative purposes. Negative pressure is a term used to describe a pressure that is below normal atmospheric pressure. Negative pressure therapy is utilized for several sites on the skin, such as a wound or an incision Furthermore, negative pressure therapy is useful to manage wounds with complex healing concerns. Additionally, negative pressure therapy could also be used for cosmetic purposes like removing wrinkles.

Generally, negative pressure therapy is achieved by maintaining a reduced pressure beneath a dressing at a dressing site.

BRIEF DESCRIPTION

According to one aspect, a negative pressure dressing includes a drape, a cover assembly, a reactor, and a sealing liner. The drape is configured to seal to skin of a patient to define a substantially air-tight enclosed volume under the drape and around a tissue site. The drape includes an aperture extending through the drape from a top surface to a bottom surface of the drape and thus providing access to the enclosed volume under the drape. The cover assembly selectively seals off the aperture in an air-tight manner to prevent a bulk flow of air from an external atmosphere through the aperture and into the enclosed volume. The cover assembly includes a base attached to the drape, and a top that is moveable with respect to the base between an opened position and a closed position. The reactor is configured to react with a selected gas found in air. The sealing liner covers the reactor and forming a first seal that prevents the reactor from being exposed to the selected gas. The first seal is configured to be selectively broken so as to expose the reactor to the selected gas. The reactor is configured to be selectively put in fluid communication with the enclosed volume so as to consume the selected gas in the enclosed volume. The top, when moved to the closed position, forms a second seal that seals off the aperture in a substantially air-tight manner to inhibit a bulk flow of air between the external atmosphere and the enclosed volume.

DETAILED DESCRIPTION

Figure 1:
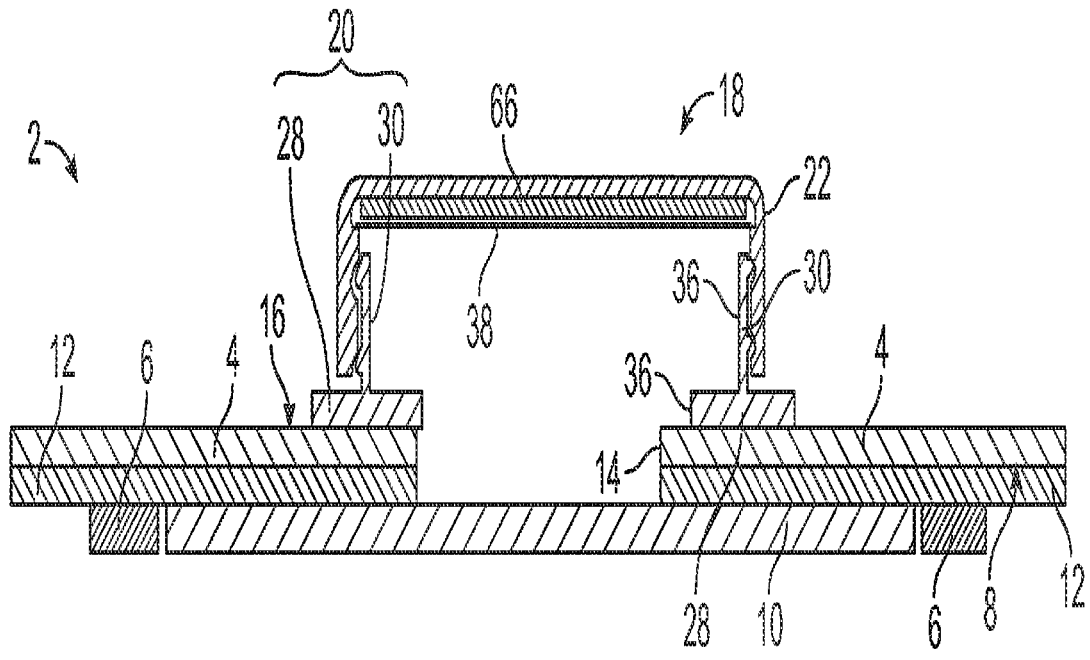
FIG. 1 is a cross section view of a dressing with cover assembly in an inactivated state according to the present subject matter.

FIG. 1 depicts a dressing 2 for negative pressure tissue treatment. The dressing 2 includes a housing 4 (also referred to herein as a "drape"), which is placed over a tissue site (i.e. skin) of a patient so as to define a substantially air-tight enclosed volume around the tissue site and beneath the drape 4. As used herein, "substantially air-tight" means that there is no bulk air flow or viscous air flow between the atmosphere and the enclosed volume, where the bulk or viscous air flow produces an equal effect on the amount of each of the different components of air (i.e. different gasses in air such as $O_2$ and $N_2$). In other words, bulk air flow is a movement of air between the atmosphere and the enclosed volume that does not change the percentages of the different gases in air in the enclosed volume, and this bulk air flow is prevented when the drape is substantially air-tight. This meaning for "substantially air-tight" is in contrast to "permeation" of gases between the atmosphere and the enclosed volume, which permeation produces, not equal but, different effects on the amount of each of the different gasses. In other words, permeation is a movement of gasses between the atmosphere and the enclosed volume that does/may change the percentages of the different gases in air in the enclosed volume, and this permeation is not prevented when the drape is substantially air-tight.

The tissue site may be, but is not limited to, a wound, an incision, or skin where there is no wound or incision. The dressing 2 can be positioned at the tissue site to enhance tissue treatment including, but not limited to, wound healing and other medical treatments, reduction of skin wrinkles and other cosmetic treatments, and other skin maladies.

Drape

The drape 4 may be a rigid drape or a flexible drape. In a non-limiting example, the drape 4 is a flexible drape. The drape 4 may be made from a flexible material including a thin, flexible, elastomeric film. Examples of such materials include polyurethane or polyethylene films. If oxygen is removed from the enclosed volume under the drape, such as by use of an oxygen scavenger (as will be discussed in more detail herein with respect to the reactor 66), the drape 4 may be capable of maintaining a low-oxygen environment (i.e. less than the 21% present in ambient air) in the enclosed volume underneath the drape 4 with use of such an oxygen scavenger. The removal of oxygen gas from the enclosed volume may also create a low-pressure environment in the enclosed volume, as will be discussed in more detail herein. For this, the dressing 2 may include internal components arranged under the flexible drape 4 that have a resistance to compression, thereby creating enough volume under the drape 4 to produce and maintain a negative pressure under the drape 4, e.g. between −25 mmHg and −160 mmHg, as a result of oxygen gas being removed by the oxygen scavenger.

The thin film from which the drape 4 is made can be substantially impermeable to liquids but somewhat permeable to water vapor, while still being capable of maintaining a low-oxygen environment in the enclosed volume underneath the drape 4 during use of an oxygen scavenger. For example, the thin film material from which the drape 4 could be made include polyurethane or other semi-permeable material such as that sold under the Tegaderm® brand or 9834 TPU tape available from 3M. Similar films are also available from other manufacturers. Even though the film from which the drape 4 is made may have a water vapor transmission rate of about 836 g/m²/day or more, these films are still capable of maintaining negative pressure and/or a low-oxygen environment for one or more hours or days in the enclosed volume underneath the drape 4 when an appropriate seal is made around the periphery of a tissue site.

The dressing 2 may include a gasket 6 at a bottom surface 8 of the drape 4 for sealing the drape 4 to the skin around the tissue site in a substantially air-tight manner, and thus, along with the drape 4 and a cover assembly 18, defines the enclosed volume around the tissue site. The gasket 6 can have a generally annular shape, and may be a silicone gel, e.g. one applied on a backing film. Other types of gasket materials may be employed, such as a hydrogel, e.g. one that is applied on a backing film. The backing film can be a polyurethane, polyethylene, polypropylene, or co-polyester film, and can be brought into contact with an adhesive layer 12 applied to the bottom surface 8 of the drape 4 in order to fix the gasket 6 to the drape 4. The gasket 6 may be robust enough for maintaining a therapeutic negative pressure in the enclosed volume around a tissue site, which therapeutic negative pressure can be between −25 and −160 mmHg with respect to atmospheric pressure. The gasket 6 may be robust enough for maintaining a pressure in the enclosed volume around a tissue site from atmospheric pressure to −160 mmHg, which pressure can be adjusted as desired, including by the use of the reactor 66.

The dressing 2 may also include a tissue site contacting layer 10 arranged within the enclosed volume and within a perimeter formed by the gasket 6, i.e. the gasket 6 may be a continuous annulus and thus radially surround the tissue site contacting layer 10 by forming a perimeter around the tissue site contacting layer 10. The tissue site contacting layer 10 may be affixed to the bottom surface 8 of the drape 4 by the adhesive layer 12, or by another adhesive layer. The tissue site contacting layer 10 may include an absorbent material, which can be made from super absorbent polymers, absorbent beads, foams, or natural absorbents. For example, the absorbent material can be a hydroactive non-woven wound pad, such as that available from Freudenberg Performance Materials, which chemically absorbs exudate and precludes the exudate from passing through the absorbent material. In a non-limiting example, the absorbent material may also be an easily compressible porous material to allow the enclosed volume under the drape 4 to decrease in size as needed to maintain internal pressure close to ambient pressure. In another non-limiting example, an internal component arranged under the drape 4, such as the tissue site contacting layer 10, may have a resistance to compression and thus maintain the size of the enclosed volume under the drape 4 so that a removal of air (or a selected gas found in air) from the enclosed volume results in a decrease in pressure in the enclosed volume. The tissue site contacting layer 10 may be designed to be relatively non-compressible, so as to maintain a size of the enclosed volume, e.g. even under a reduced pressure inside the enclosed volume.

The tissue site contacting layer 10 can also be designed to allow for a bulk flow of air through it and for contacting a wound, and can be made of an elastomeric material, such as a polymeric material that has rubber-like properties. The elastomeric material of the tissue site contacting layer 10 can be a thin, flexible elastomeric film. Some examples of such material include a silver coated nylon, a perforated silicone mesh, or other materials that will not stick to the tissue site of a patient. If desired, antibacterial or antimicrobial materials may be deposited on/in the tissue site contacting layer 10.

Figure 2:
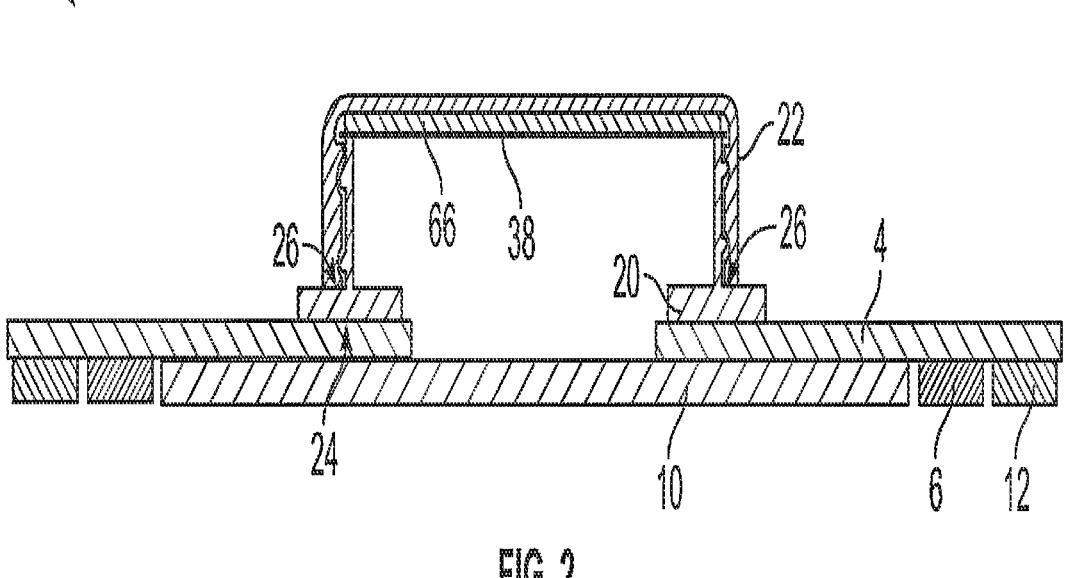
FIG. 2 is a cross section view of a dressing with cover assembly in an activated state according to the present subject matter.
Figure 3:
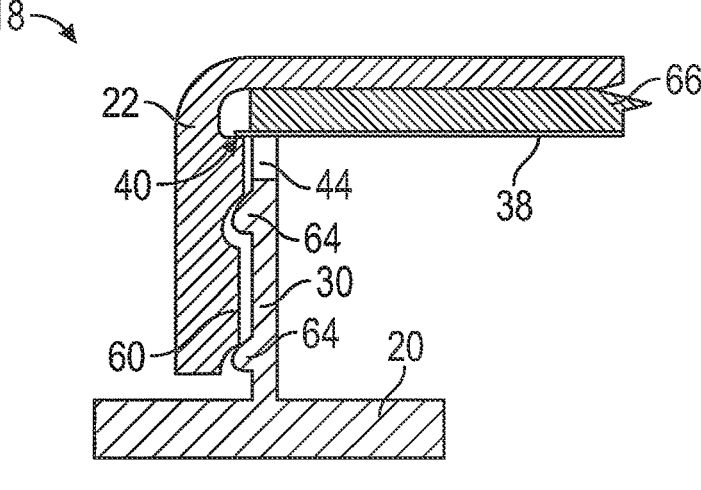
FIG. 3 is a cross section detailed view of a portion of a cover assembly in an inactivated state according to the present subject matter.
Figure 18:
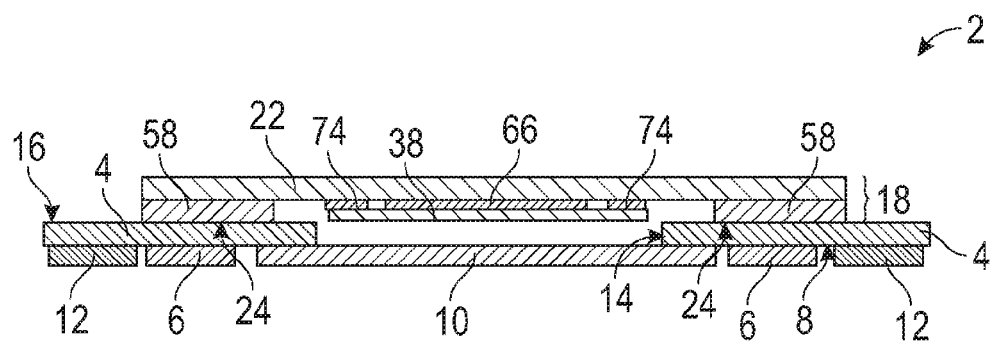
FIG. 18 is a cross section view of the dressing of FIG. 15 along line A-A.

The dressing 2 may include an adhesive layer 12 applied to the bottom surface 8 of the drape 4. The adhesive layer 12 may be applied by flood coating to cover the entire bottom surface 8 of the drape 4 (FIG. 1), or applied to select portions of the bottom surface 8 (FIGS. 2 and 18). The adhesive layer 12 may be used to adhere the tissue site contacting layer 10 to the bottom surface 8 of the drape 4 and the drape 4 to the skin, thus adhering the dressing 2 to the skin of a patient around the tissue site (FIG. 1). The gasket 6 may also be applied to the adhesive layer 12, so as to leave a margin of the adhesive layer 12 annularly surrounding the gasket 6, which margin may be used to adhere the dressing 2 to skin (FIG. 1). Alternatively, the gasket 6 and the tissue site contacting layer 10 may be applied directly to the bottom surface 8 of the drape 4 with a different adhesive(s), and in this case the adhesive layer 12 may be applied as an annulus around the perimeter of the gasket 6 (FIGS. 2 and 18). The adhesive layer 12 may be a pressure-sensitive acrylic-based adhesive. Other types of adhesives could be used, however, a pressure-sensitive acrylic-based adhesive is known to provide strong initial tack to skin that can last for a relatively long time, for example a few days, when in contact with the skin. The pressure-sensitive acrylic-based adhesive can be applied over an entirety of the of the bottom surface 8 of the drape 4 (FIG. 1) or only to select portions of the bottom surface 8 (FIGS. 2 and 18).

Also, it is well known that typical adhesives, in particular pressure-sensitive acrylics such as those adhering the drape 4 to the patient's skin, do not form air-tight seals with skin. Thus, the drape 4 may be well adhered to the skin by the adhesive layer 12, but may still allow ambient air to enter between the drape 4 and the skin into the enclosed volume beneath the drape 4. For example, hair follicles and other irregularities on the skin may prohibit an adhesive from forming an adequate air seal between the drape 4 and the skin, thus preventing the enclosed volume from reaching what is often considered to be a therapeutic negative pressure, which is typically between −25 and −160 mmHg, as the selected gas is being removed from the enclosed volume by the reactor 66. These "leaks" of air flowing past the adhesive layer 12 may be overcome either by including the gasket 6, which forms a substantially air-tight seal between the dressing 2 and the skin, or when the reactor 66 has sufficient capacity to maintain the low-oxygen environment even when these leaks exist. In other circumstances not involving adhering to skin, it is noted that typical adhesives are able to form air-tight seals between two polymer materials. Therefore, typical adhesive may be used to form air-tight seals 24, 26 (discussed herein) between two polymer components of the dressing 2.

The dressing 2 may include a release liner (not shown) disposed on the bottom of the dressing 2 to cover the exposed adhesive layer 12, the gasket 6, and the tissue site contacting layer 10, and inhibit contamination of these. The release liner is removed before the dressing 2 is applied to the tissue site. When the release liner is removed, the gasket 6, the adhesive layer 12 in the margin surrounding the gasket 6, and the tissue site contacting layer 10, are exposed. As the dressing 2 is placed on the patient, the adhesive layer 12, which can be an acrylic-based adhesive that is distinct from the gasket 6 (if provided), secures the drape 4 to the patient's skin around the tissue site.

The drape 4 includes an aperture 14, which is a through hole that extends completely through the drape 4 from the top surface 16 of the drape 4 to the bottom surface 8 of the drape 4. The aperture 14 is arranged inside the perimeter formed by the gasket 6, and thus provides access into the enclosed volume. The aperture 14 may have any size as desired, obviously as long as it is smaller than the size of the drape 4. For example, the aperture 14 in FIGS. 12-18 may be bigger, relative to the size of the drape 4, than the aperture 14 in FIGS. 1-11.

The drape 4 can be made from a material that is air impermeable to bulk or viscous air flow so that air is precluded or greatly inhibited from entering into the enclosed volume by bulk or viscous flow. A reactor 66 can be in fluid communication with the enclosed volume and thus can consume a selected gas within the enclosed volume, thus reducing the partial pressure of the consumed gas within the enclosed volume, and also possibly reducing the total gas pressure within the enclosed volume when the drape 4 is rigid or otherwise has internal components resistant to compression. The drape 4 could also be made from materials that allow for some level of permeation of gases through the drape 4. The drape 4 can be formed of a material that is at least partially gas permeable for certain gasses (e.g., oxygen or nitrogen gas permeable) to allow the gas(es) to permeate between the tissue site in the enclosed volume and the atmosphere.

Cover Assembly

The dressing 2 includes a cover assembly 18 arranged on the top surface 16 of the drape 4, and which can be sealed over the aperture 14 in a substantially air-tight manner. The cover assembly 18 can include any of a base 20, a top 22, a reactor 66, and a sealing liner 38. The top 22 may be round (FIGS. 1-6 and 11), rectangular (FIGS. 12-18), or other shapes as desired, and the base 20 may have a corresponding shape to the top 22. The cover assembly 18 and its through hole 36, if present, may have different sizes with respect to the size of the drape 4 and the size of the aperture 14. The cover assembly 18 has a size large enough to seal the aperture 14, and for this purpose may be made from a material that is air impermeable, such as acrylonitrile butadiene styrene (ABS) plastic.

Base

The base 20 is optionally included to cooperate with the top 22 to seal off the aperture 14 in the drape 4. The base 20 may include a lower base portion 28 and an upper base portion 30, which may be integral to each other and thus form a one-piece base 20, or may be two separate pieces that are connected together to form a two-piece base 20. The lower base portion 28 is attached to and sealed at a first seal 24 to the drape 4, and the upper base portion 30, if present, mates with and connects to the top 22 to create a second seal 26 between the top 22 and the base 20, thus sealing the aperture 14.

Figure 11:
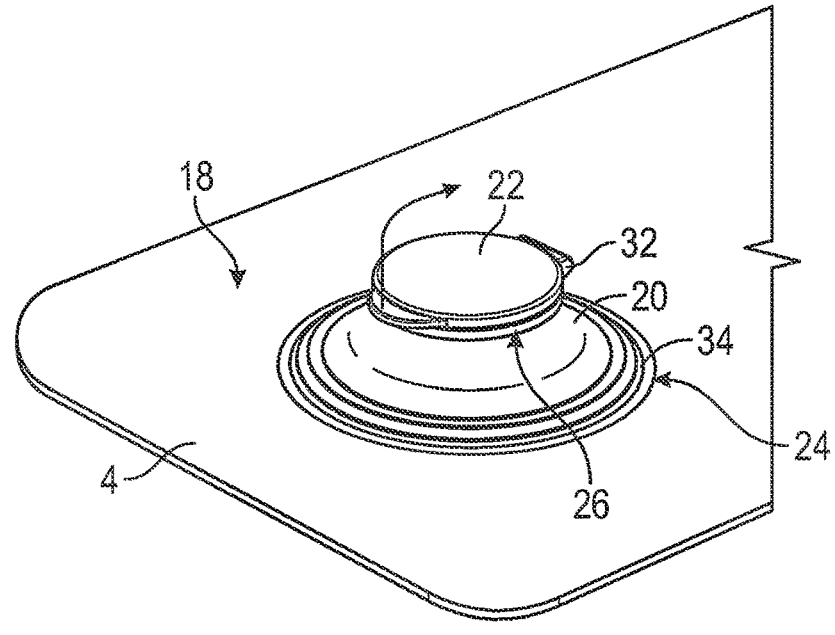
FIG. 11 is a perspective view of dressing including a cover assembly having a rigid flip cap according to the present subject matter.
Figure 12:
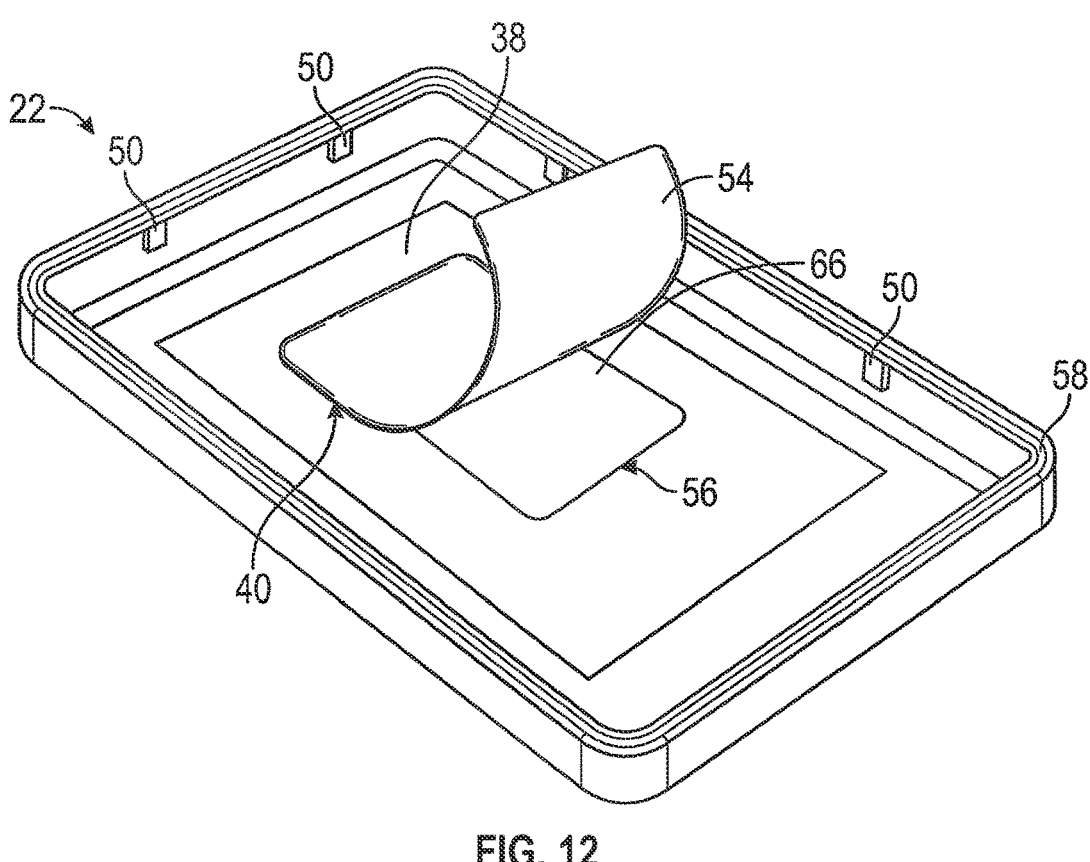
FIG. 12 is a bottom perspective view of a top of a cover assembly with an release liner removed from covering a reactor according to the present subject matter.
Figure 13:
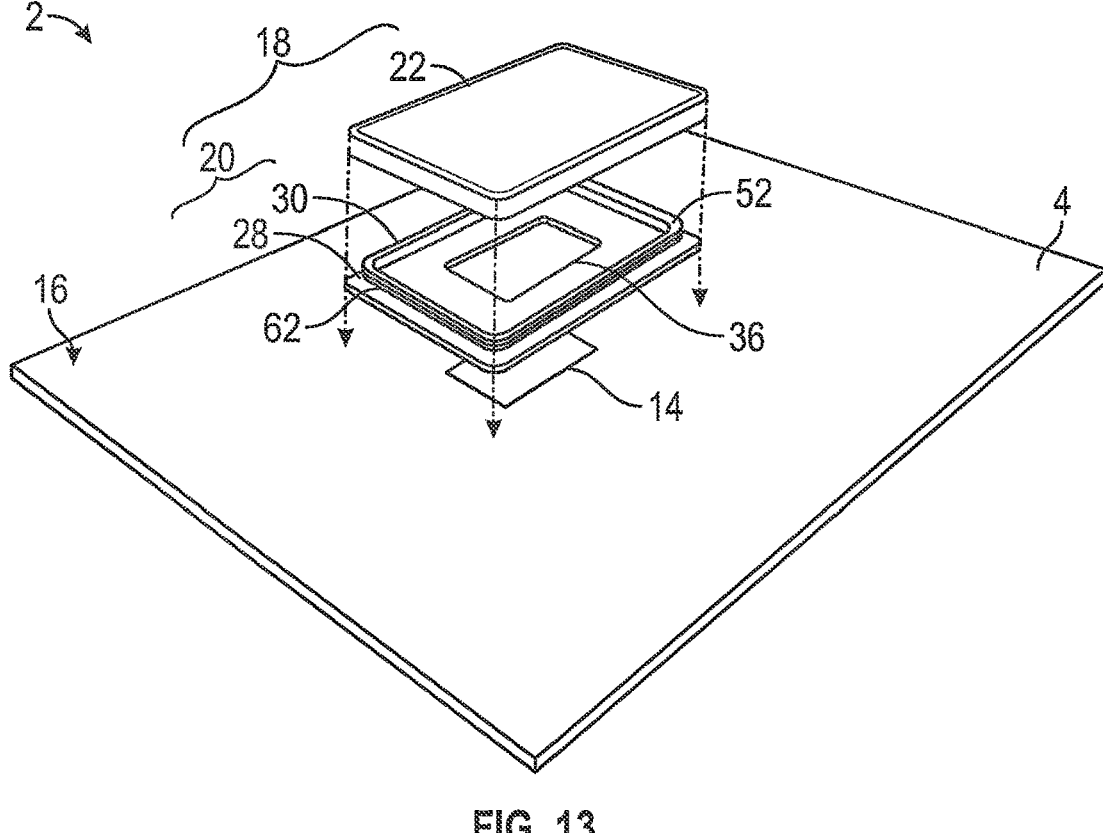
FIG. 13 is a perspective view of assembling a dressing including a cover assembly according to the present subject matter.
Figure 14:
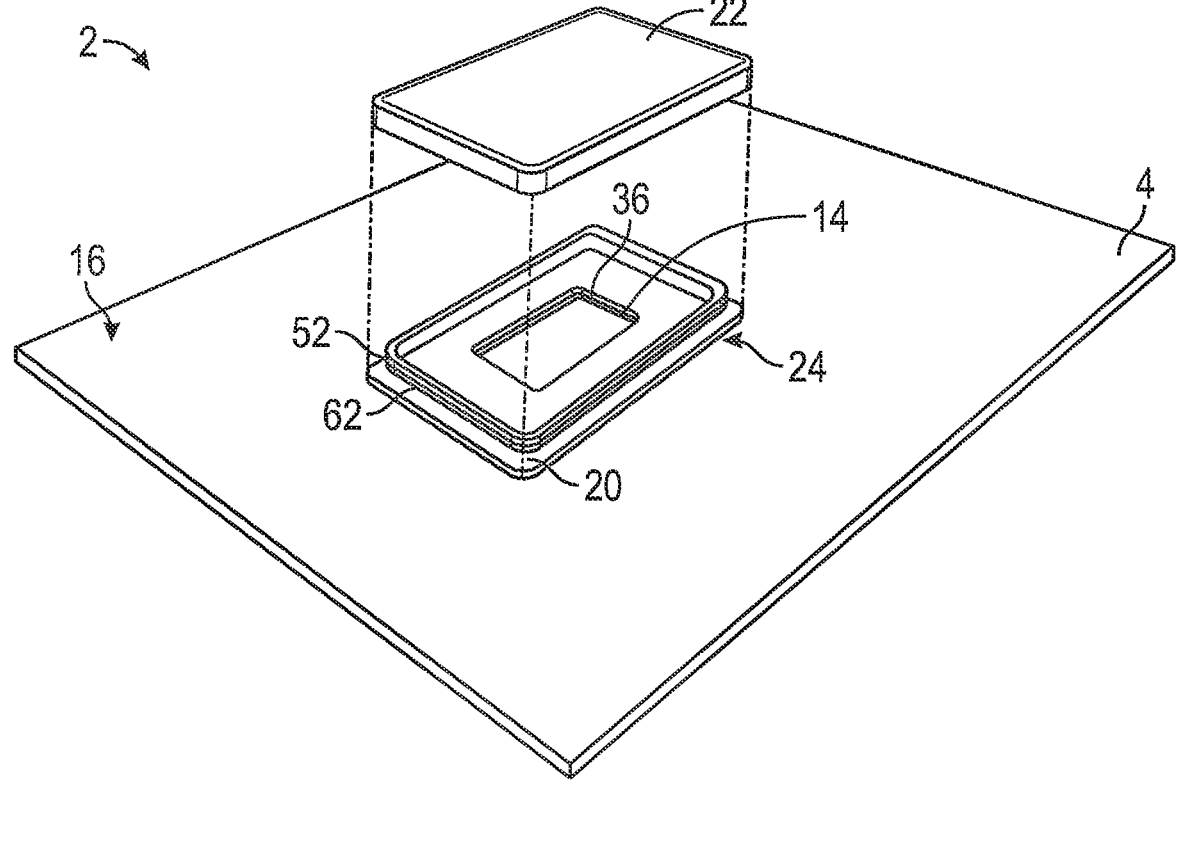
FIG. 14 is a perspective view of connecting a top to a base of a cover assembly according to the present subject matter

As shown in FIGS. 1-6, the top 22 is connectable to the base 20, by screwing onto the upper base portion 30. As shown in FIG. 11, the top 22 is integrally connected to the base 20 as an integral flip top that opens and closes by rotating (see arrow in FIG. 11) around a hinge 32, and snaps onto the upper base portion 30 by a compression or friction fit. In FIGS. 12-14, the top 22 is separate from, but connectable to, the base 20, and is snapped onto the base 20 by engagement of barbs 50 in the top 22 with a ridge 52 on the base 20. The ridge 52 is arranged over an indentation 62, in which the barbs 50 can be arranged. As shown in FIGS. 12-14, the top 22 is in the form of a rectangular cap, and includes the barbs 50 on its inside surface. When the top 22 is brought down onto and mated with the base 20 (as shown by hashed lines in FIG. 14), the barbs 50 pass over the ridge 52, fit into the indentation 62 on the upper base portion 30 under the ridge 52, and thus hold the top 22 onto the base 20. The second seal 26 may form between an upper surface of the upper base portion 30 and an inside lower surface of the top 22, between a lower surface of the top 22 and an upper surface of the lower base portion 28, between other surfaces of the top 22 and base 20, or combinations thereof, and may be formed with an O-ring, gasket, or other sealing structure compressed between these surfaces. As shown in FIG. 12, the cap 22 has a gasket/adhesive 58 on a bottom surface of the cap 22, which forms a seal against a top surface of the lower base portion 28 when the cap 22 is joined/mated with the base 20. In each of these embodiments, the top 22 seals against the base 20, e.g. against the lower base portion 28, to create the second seal 26. Other connection arrangements can be used to connect and seal the top 22 to the base 20.

The lower base portion 28 is sealed to the top surface 16 of the drape 4 in a substantially air-tight manner at the first seal 24. This may be accomplished by using a base adhesive and/or an adhesive tape 34, either one or both providing adhesion and/or the substantially air-tight first seal 24 to the top surface 16. The base adhesive may be arranged between the lower base portion 28 and the drape 4, and can adhere the lower base portion 28 to the drape 4. The adhesive tape 34 may adhere to the top surface 16 of the drape 4 and may cover over part of the lower base portion 28, e.g. adheres to an upper surface of a perimeter/edge of the lower base portion 28 and to the top surface 16 of the drape 4 (see FIG. 11). Although not shown, the lower base portion 28 could alternatively be arranged inside the enclosed volume under the drape 4, while the upper base portion 30 could then stick up through the aperture 14 out of the enclosed volume, and the lower base portion 28 could be sealed with the adhesive layer 12 to the bottom surface 8 of the drape 4 to create the first seal 24.

The lower base portion 28 and the upper base portion 30 define a through hole 36. The base 20 is generally aligned over the aperture 14 so that the lower base portion 28 completely radially surrounds the aperture 14 and seals to the top surface 16 of the drape 4 completely around the perimeter of the aperture 14. The lower base portion 28 is attached to the drape 4 such that the through hole 36 is in fluid communication with the aperture 14, e.g. aligned directly over the aperture 14.

When the top 22 is in an opened position, the aperture 14 and the through hole 36 together create a channel for bulk air flow between the enclosed volume and the atmosphere that is exterior of the dressing 2.

Figure 17:
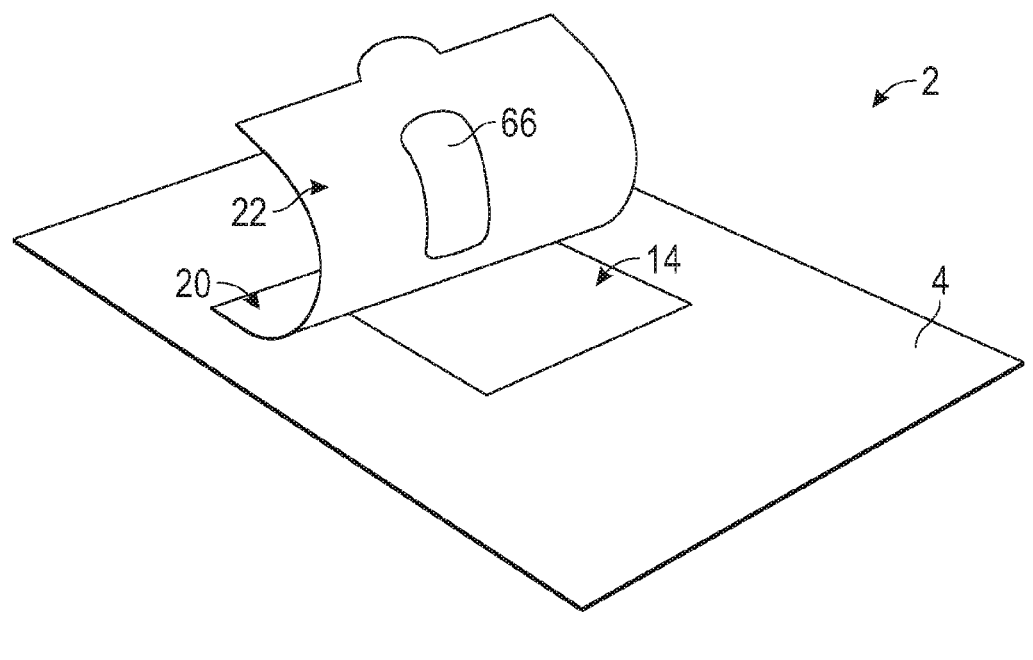
FIG. 17 is a perspective view of the dressing of FIG. 16 with the sealing liner removed to expose the reactor.

In FIGS. 15-18, the cover assembly 18 includes the top 22 and the base 20, which together are a one-piece sealing film, and in which the top 22 portion is configured to be peeled away from the drape 4 while the base is configured to remain attached to the drape 4. The single piece film of the top 22 and base 20 are sealed to the top surface 16 of the drape 4 with an adhesive 58. The portion of the adhesive 58 under the top 22 may be removable from and resealable to the drape 4, while the portion of the adhesive 58 under the base 20 may be permanent. However, this is not required and the entire adhesive 58 may be removable/resealable to the drape 4 so as to allow replacement of the cover assembly 18, such as when the reactor 66 is used up and a new reactor 66 is desired. In order to activate the reactor 66, the top 22 is peeled away from the top surface 16 of the drape 4 to exposed the aperture 14 and the sealing liner 38 arranged on an underside of the top 22 (FIG. 16), while the base 20 remains attached to the drape 4, e.g. to keep a relative alignment with the drape 4. The sealing liner 38 is then pulled off the underside of the top 22 to exposed the underlying reactor 66 (FIG. 17). The top 22 is then sealed back against the top surface 16 of the drape 4 via the adhesive 58 to put the reactor 66 in fluid communication with the enclosed volume via the aperture 14 so as to consume the selected gas within the enclosed volume. In this example, the single-piece film of the top 22 and base 20 is sealed to the top surface 16 of the drape 4 via the adhesive 58 to create air-tight seals 24, 26 around the aperture 14

Top

With reference to FIGS. 1-6 and 11-14, the top 22 and base 20 cooperate to provide the second seal 26, which along with the first seal 24 operates to seal the aperture 14 in a substantially air-tight manner to inhibit the bulk flow of air between the enclosed volume to the external atmosphere, which is the atmosphere external to the dressing 2 and enclosed volume under the dressing 2. The top 22 may be a rigid or flexible cap, that is connected to the base 20 to provide this air-tight seal and thus cut off the channel between the enclosed volume and the external atmosphere, and can be removed from the base 20 to open the channel between the enclosed volume and the external atmosphere. In other words, the cap 22 is configured to open in order to allow a bulk flow of air through the aperture 14 and the through hole 36 between the enclosed volume and the external atmosphere, and to close in order to restrict a bulk flow of air through the through hole 36 between the enclosed volume and the external atmosphere, but allow a bulk flow of air through the aperture 14 between the enclosed volume and the reactor 66 on the underside of the cap 22.

The cap 22 may be integrally connected with the base 20 by a moveable joint so that the cap 22 can move relative to the base 20 between an opened position and a closed position but not become completely disconnected from the base 20. The moveable joint between the cap 22 and the base

20 may include a hinge 32 (FIG. 11), a lanyard, or other type of mechanism that provides a moveable joint between the cap 22 and the base 20. The cap 22 and the base 20 may both be part of a one-piece component (FIG. 11) and thus are integrally connected by the moveable joint, such as a one-piece flexible film (FIGS. 7-10) defining the moveable joint between the cap 22 and base 20.

Where the cover assembly 18 includes the hinge joint (FIG. 11), the cap 22 and base 20 may be a one-piece construction including the hinge 32. The hinge 32 may also be a distinct component from the cap 22 and base 20. In this configuration, the cap 22 may be moved relative to the base 20 between the opened position and the closed position by swinging the cap 22 about the hinge 32 (see arrow in FIG. 11).

Figure 4:
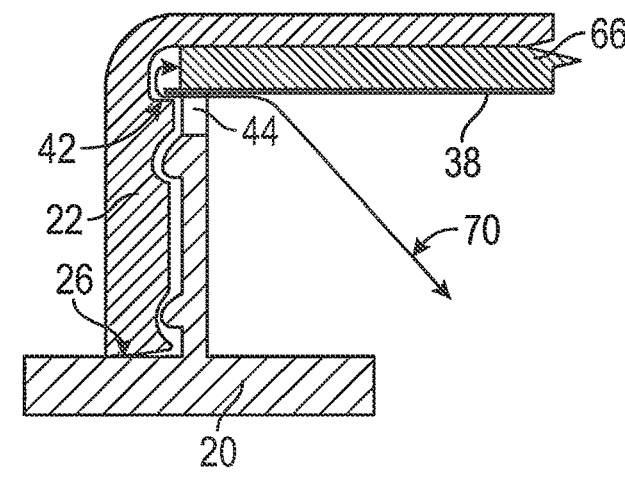
FIG. 4 is a cross section detailed view of a portion of a cover assembly in an activated state according to the present subject matter.
Figure 5:
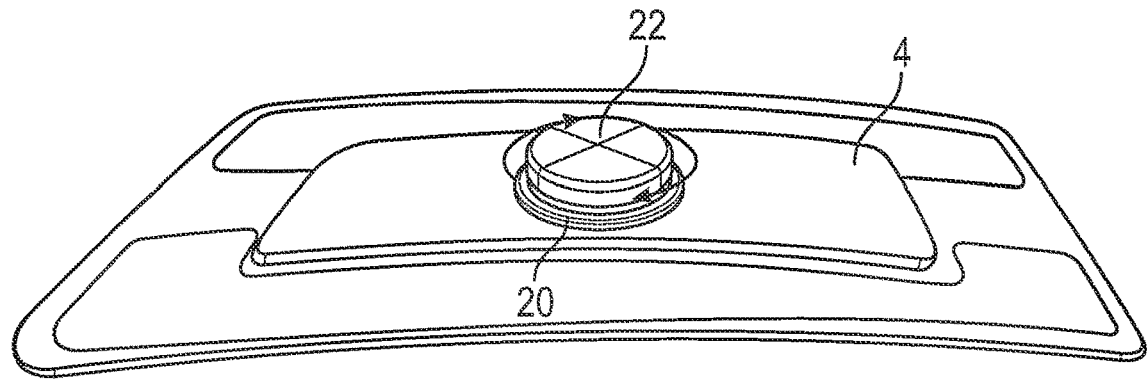
FIG. 5 is a perspective view of a dressing with a cover assembly according to the present subject matter.

The second seal 26 in FIGS. 1-6 and 11-14 may be made by an O-ring, gasket, or other sealing structure on the cap 22 and/or on the base 20. The O-ring, gasket, or other sealing structure may be compressed between the cap 22 and the base 20 when the cap 22 is in the closed position (FIGS. 2, 4, 11).

The cap 22 and the base 20 may be selectively joined to seal off the aperture 14 and the through hole 36, by a threaded joint (FIGS. 1-6), a compression or friction fit (FIG. 11), a snap joint (FIGS. 13-14), or by other joints. Where the cover assembly 18 includes a threaded joint, the cap 22 and the base 20 may be distinct components, and may be joined by mating threads 60 on the cap 22 and threads 64 on the upper base portion 30. In this configuration, the cap 22 may be moved relative to the base 20 between the opened position and the closed position by turning the cap 22 relative to the base 20 (See arrows in FIG. 5), and when moved to the opened position may be completely separated from the base 20. The opened position and the closed position may be separated by turning the cap 22 with respect to the base 20, e.g. by a quarter turn of the cap 22, or more or less.

The cap 22 may be moved from the closed position to the opened position by turning the cap 22 relative to the base 20 in one direction (e.g. counter clockwise, FIGS. 1-6), or by pulling the cap 22 up away from the base 20 (FIGS. 11-14), which moves the cap 22 up away from the upper base portion 30, thus breaking the second seal 26 such that the second seal 26 no longer seals the through hole 36. This unsealing of the through hole 36 allows air to flow through the cover assembly 18 and in and out of the aperture 14 between the external atmosphere and the enclosed volume. The cap 22 may be moved from the opened position to the closed position by turning the cap 22 relative to the base 20 in the other direction (e.g. clockwise, FIGS. 1-6), or by pushing the cap 22 back down onto the base 20 (FIGS. 11-14), which moves the cap 22 down toward the base 20, thus pinching. e.g. an O-ring, between the base 20 and the cap 22 such that the O-ring touches the cap 22 and the base 20, thus creating the second seal 26 between the cap 22 and the base 20. This seals the through hole 36, thus inhibiting a bulk flow of air through the through hole 36 between enclosed volume and the external atmosphere that is external to the drape 4.

With reference to FIGS. 7-10, the base 20 and top 22 are integral, and may be in the form of a one-piece flexible sealing film. A first end of the sealing film constitutes the base 20, and is attached to the top surface 16 of the drape 4, and the opposite second end of the sealing film constitutes the top 22, which may initially extend away from the drape 4 (FIGS. 7 and 8) in an opened position. The top 22 of the sealing film may be covered by a release liner 48. The release liner 48 may cover a bottom adhesive surface of the top 22 of the sealing film and is selectively removeable from the bottom adhesive surface. The release liner 48 may be removed from the bottom adhesive surface of the top 22 of the sealing film (FIG. 9), and the top 22 of the sealing film may then be moved relative to the base 20 to a closed position (FIG. 10) and selectively sealed directly to the top surface 16 of the drape 4 so as to form the second seal 26 that seals off the aperture 14. The second seal 26 may completely surround the aperture 14 and thus close off the aperture 14 in a substantially air-tight manner. A moveable joint between the top 22 of the sealing film and the base 20 of the sealing film may be constituted by a fold or bend in the sealing film.

Figure 15:
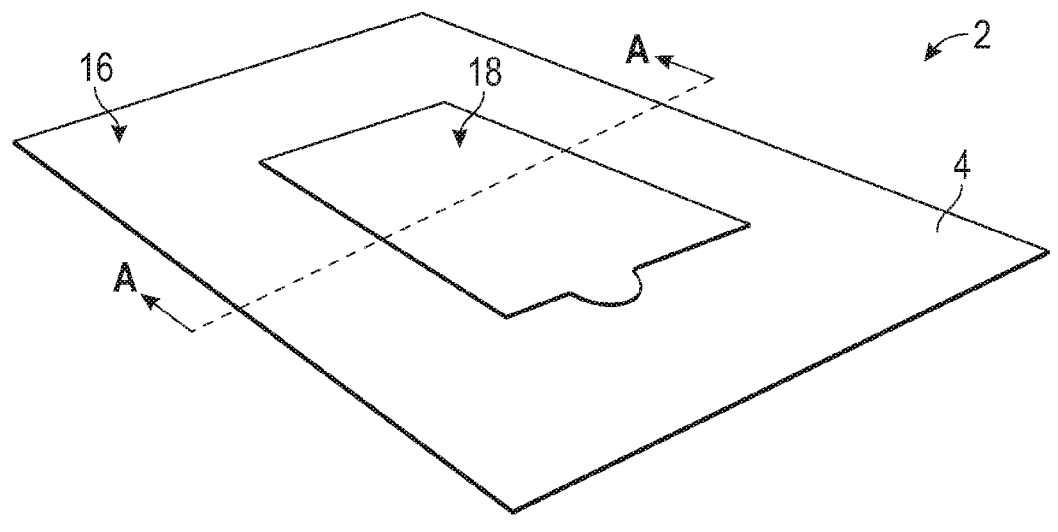
FIG. 15 is a perspective view of a dressing according to the present subject matter.
Figure 16:
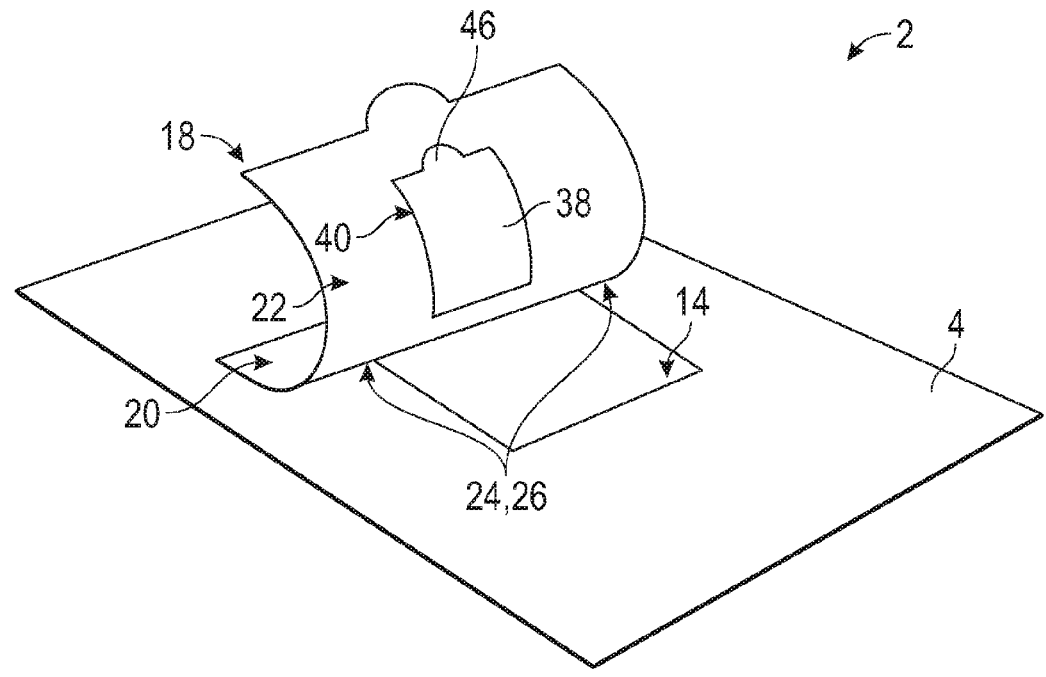
FIG. 16 is a perspective view of the dressing of FIG. 15 with the cover assembly pulled up away from the drape.

With reference to FIGS. 15-18, the top 22 and the base 20 are integral with each other as a one-piece sealing film, and thus together forming an air-tight seal 24, 26 to the top surface 16 of the drape 4 via the adhesive 58. A first end of the sealing film constitutes the base 20, and is attached to the top surface 16 of the drape 4, and the opposite second end of the sealing film constitutes the top 22, which may initially be sealed to the top surface 16 like the base 20 in a closed position (FIG. 15). The top 22 of the sealing film may then be moved relative to the base 20 to an open position (FIG. 16) and the sealing liner 38 may be removed to expose the reactor 66. The top may then be selectively sealed back directly to the top surface 16 of the drape 4 in the closed position (FIG. 15) so as to form the second seal 26 that seals off the aperture 14 along with the first seal 24 formed by the base 20 and put the reactor 66 in fluid communication with the enclosed volume. The first seal 24 and the second seal 26 may together completely surround the aperture 14 and thus close off the aperture 14 in a substantially air-tight manner. A moveable joint between the top 22 and the base 20 of the one-piece sealing film may be constituted by a fold or bend in the one-piece sealing film.

Reactor

The dressing 2 for tissue treatment may also include a reactor 66 (FIGS. 1-4 and 8-10). The reactor 66 is configured to react with (e.g. consume) a selected gas (e.g., nitrogen, oxygen, carbon dioxide) found in air. As the reactor 66 consumes the selected gas from air within the enclosed volume, the total gas pressure within the enclosed volume may be reduced. For example, where the reactor 66 is an oxygen scavenger and thus consumes oxygen in the enclosed volume, and where the reactor 66 is under a rigid drape 4 or under a flexible drape 4 that is supported by internal components that are resistant to compression, then there can be an approximate 20% reduction from total gas pressure in the enclosed volume, which is explained in more detail below. If the reactor 66 is under a flexible drape 4 that is not supported by internal components that are resistant to compression, then the drape 4 may collapse as oxygen is consumed by the reactor 66, and if the enclosed volume decreases in size in an amount corresponding to the amount of oxygen consumed, then a decrease in the total gas pressure within the enclosed volume may not occur, but a low-oxygen environment may still arise.

The reactor 66 may be put into fluid communication with the enclosed volume so as to consume (react with) the selected gas from the enclosed volume. The selected gas may be oxygen, and thus when the reactor 66 is used, it may generate a low-oxygen environment in the enclosed volume and around the tissue site.

When the dressing 2 is initially applied to skin to create the enclosed volume around the tissue site, and the reactor 66 is activated to consume the selected gas (e.g. oxygen) from the enclosed volume, it may be that, although a low-oxygen environment is created in the enclosed volume, relatively little negative pressure is initially developed within the enclosed volume. This may be because of the flexibility of the drape 4, which, even though there are internal components resistant to compression, may still collapse somewhat as the oxygen is consumed. Thus, while nearly all the oxygen is removed by the reactor 66 from the enclosed volume, and thus the total gas is reduced by about 20%, the volume shrinkage prevents a significant or any noticeable pressure reduction in the enclosed volume. However, after the oxygen is consumed from the enclosed volume, the air inside the enclosed volume no longer has a ratio of 80/20 of nitrogen to oxygen, and instead, the air inside the enclosed volume is nearly all nitrogen and no oxygen. Because of this, the partial pressure of nitrogen within the enclosed volume is higher than the partial pressure of nitrogen outside the enclosed volume in the external atmosphere. This imbalance in the partial pressures of nitrogen between the enclosed volume and the external atmosphere in a flexible drape 4 that is collapsible, drives the permeation of nitrogen gas out of the enclosed volume, through the drape, and to the external atmosphere. This permeation of nitrogen out of the enclosed volume is driven by the consumption of oxygen within the enclosed volume by the reactor, a collapse of the flexible drape from the consumption of oxygen (which reduces the size of the enclosed volume), and a resultant increase in the partial pressure of nitrogen within the smaller enclosed volume. The nitrogen permeating out of the dressing results in a further reduction of the total gas pressure within the enclosed volume, which may reach near −160 mmHg, especially where a full collapse of the drape 4 is prevented by internal components resistant to compression. In a rigid drape 4 that does not experience any significant collapse, the consumption of oxygen from the enclosed volume may not change or significantly change the partial pressure of nitrogen within the enclosed volume. This is because the size of the enclosed volume and the amount of nitrogen within the rigid drape 4 do not change or do not substantially change. In this scenario, there will be about a 20% reduction in the volume of air in the enclosed volume due to the consumption of all the oxygen from the air in the enclosed volume, which may result in the total gas pressure in the enclosed volume reaching −25 to −160 mmHg. However, since all of the oxygen in consumed within the enclose volume, the partial pressure of oxygen within the enclosed volume is less than the outside atmosphere. This difference may cause permeation of oxygen through the rigid drape 4 and into the enclosed volume. However, this oxygen that permeates into the enclosed volume is subsequently consumed by the reactor, thus maintaining the reduce pressure within the enclosed volume.

The reactor 66 may be put into fluid communication with the enclosed volume via the aperture 14 (FIGS. 1-6 and 11-18), wherein the reactor 66 is external to the enclosed volume, or may be put into fluid communication with the enclosed volume by being arranged within the enclosed volume (FIGS. 7-10). If external to the enclosed volume, the reactor 66 may be arranged as part of the cover assembly 18, e.g. inside the top 22 (FIGS. 1-6 and 11-18).

The reactor 66 may be protected from exposure to the selected gas by a sealing liner 38, which may be a metal foil layer or metal foil packet. The sealing liner 38 may prevent the selected gas from reaching the reactor 66, and in this state the reactor 66 is considered not activated. To activate the reactor 66 (e.g. to expose the reactor 66 to the selected gas), the sealing liner 38, or a portion thereof, may be removed from covering the reactor 66, the sealing liner 38 may be broken, or a third seal 40 of the sealing liner 38 may be broken.

With reference to FIGS. 1-4, 6 and 11-18, the sealing liner 38 may be arranged in/on the cap/top 22 along with the reactor 66, to cover a bottom surface of the reactor 66 and thereby seal the reactor 66 from exposure to air. This may be accomplished by a third seal 40 formed between the sealing liner 38 and an inside surface of the cap 22 (FIGS. 1-4, 6, 11, and 15-18), or between the sealing liner 38 and a removable portion 54 of the sealing liner 38 (FIGS. 12-14).

In FIGS. 1-6, the third seal 40 of the sealing liner 38 is broken by rotating the cap 22 with respect to the base 20. Such rotation of the cap 22 causes the sealing liner 38 to be pressed down onto the upper base portion 30 of the base 20, which pushes the sealing liner 38 away from the inside surface of the cap 22 to which it is sealed (compare between FIGS. 3 and 4). This may break the third seal 40 and thus expose the reactor 66 to the selected gas in the enclosed volume. The broken seal 42 (FIG. 4) and an opening(s) 44 in the upper base portion 30 allow the selected gas to flow 70 from the enclosed volume, past the sealing liner 38, and to the reactor 66. Because the reactor 66 is now in fluid communication with the enclosed volume through the aperture 14, the reactor 66 reacts with the selected gas in the enclosed volume by consuming the selected gas.

Figure 6:
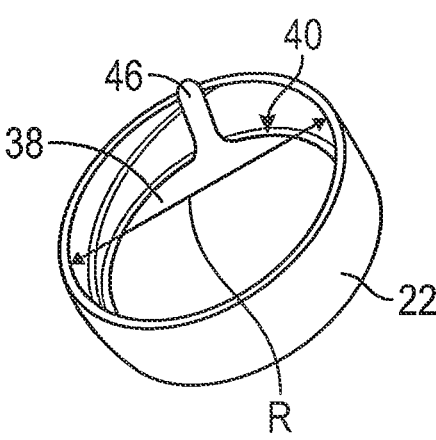
FIG. 6 is a perspective view of a cover assembly according to the present subject matter.

With reference to FIG. 6, the base 20 and the cap 22 may be identical to those shown in FIGS. 1-5, except for the process used to break the third seal 40. In FIG. 6, the third seal 40 of the sealing liner 38 may be broken by peeling the sealing liner 38 away from the inside surface of the cap 22 to which it is sealed. The sealing liner 38 may include a finger tab 46 for this purpose. The reactor 66, which may lie underneath the sealing liner 38, is thus exposed to the selected gas. The cap 22 is then screwed onto the base 20, thus putting the reactor 66 into fluid communication with the enclosure volume and allowing the reactor 66 to consume the selected gas in the enclosed volume.

With reference to FIG. 11, the base 20 and the cap 22 may be similar to those shown in FIGS. 1-6, and the third seal 40 may be broken by either pushing the cap 22 down onto the base 20 similar to what is done in FIGS. 1-5 but without twisting the cap 22, or by peeling the sealing liner 38 away from the cap 22 as is done in FIG. 6. In any of FIGS. 1-6 and 11, the cap 22 (including the reactor 66 and sealing liner 38) or just the reactor 66, may be replaced when the reactor 66 is used up and another reactor is needed.

In FIGS. 12-14, the third seal 40 of the sealing liner 38 is broken by peeling away the removable portion 54 from the rest of the sealing liner 38, thus uncovering an opening 56 in the sealing liner 38. With the third seal 40 broken and the opening 56 uncovered, the reactor 66 is thus exposed to a bulk flow of air through the opening 56 and to the reactor 66. The removable portion 54 is peeled away before the cap 22 is mated with the base 20. When this is done, the reactor 66 is now in fluid communication with the enclosed volume through the opening 56 and the aperture 14, and the reactor 66 reacts with the selected gas in the enclosed volume by consuming the selected gas.

Figure 7:
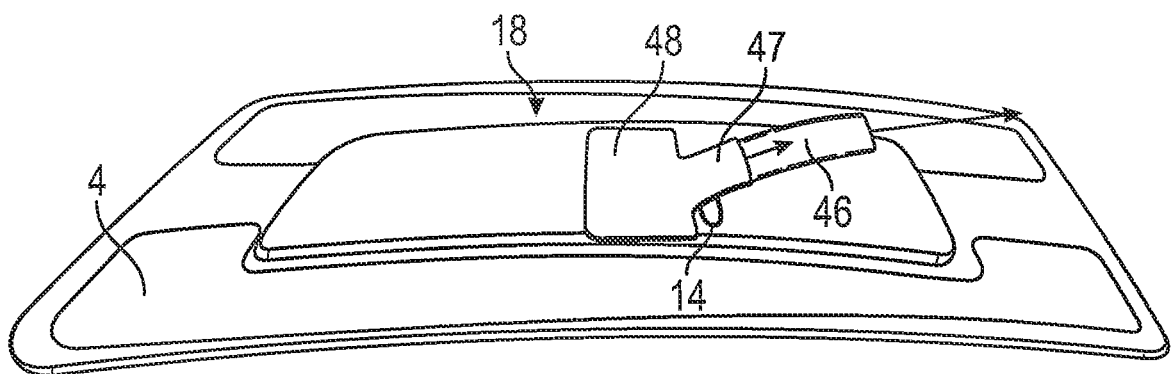
FIG. 7 is a perspective view of a dressing with a cover assembly according to the present subject matter.
Figure 8:
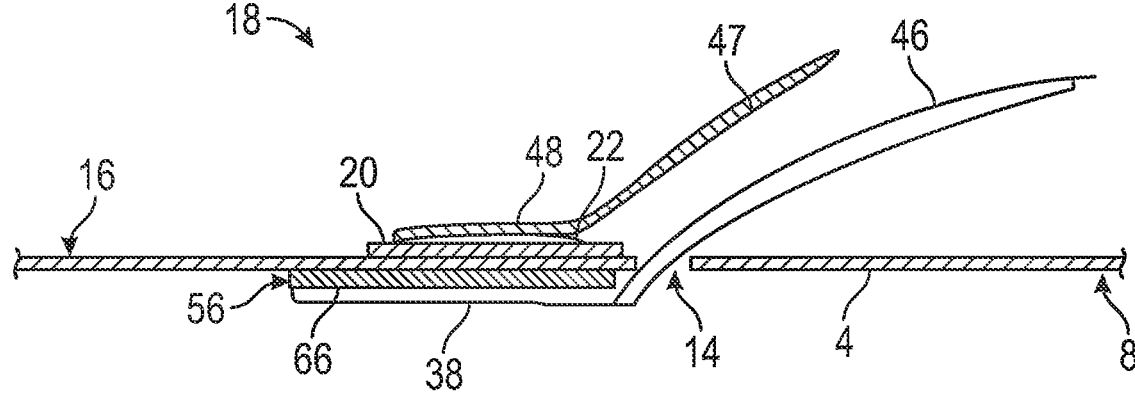
FIG. 8 is a cross section detailed view of a dressing with a cover assembly in an inactivated state.
Figure 9:
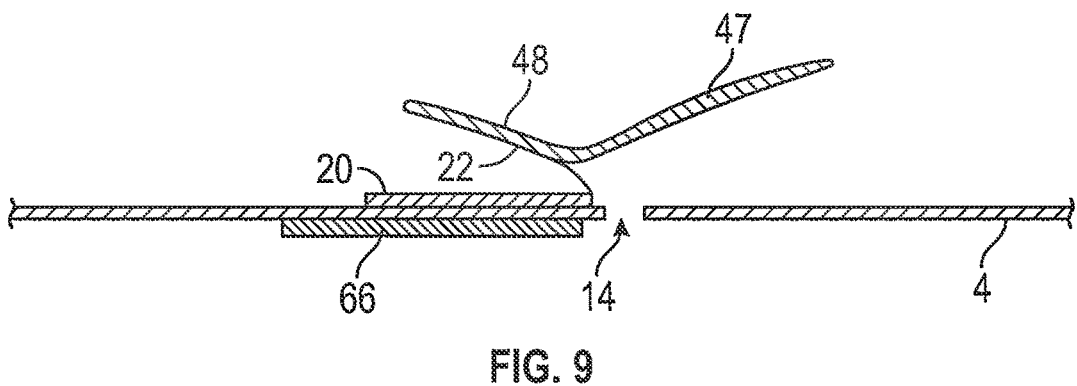
FIG. 9 is a cross section detailed view of the dressing with a cover assembly in an activated state.
Figure 10:
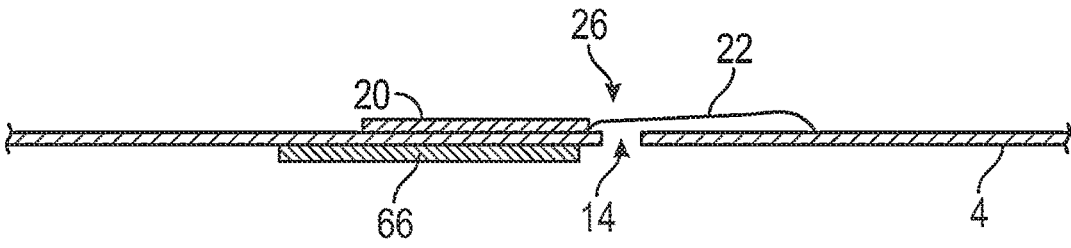
FIG. 10 is a cross section detailed view of the dressing with a cover assembly in an activated state and having a sealed aperture.

With reference to FIGS. 7-10, the reactor 66 may be arranged within the enclosed volume and activated via the aperture 14. In FIG. 7, which shows the dressing 2 in an inactivated state, the aperture 14 is a slit in the drape 4, through which the sealing liner 38 extends from the enclosed volume to the external atmosphere. The reactor 66 is arranged inside the enclosed volume, e.g. attached to an underside of the drape 4. A finger tab 46 of the sealing liner 38 may be pulled (see arrow in FIG. 7), which results in the sealing liner 38 being removed from covering the reactor 66 and thus breaking the third seal 40 and exposing the reactor 66 to the selected gas in the enclosed volume. The sealing liner 38 can be pulled all the way out of the enclosed volume through the aperture 14 and discarded. A release liner 48 can be attached to the top 22, which is in the form of a flexible sealing film 22. A second finger tab 47 of the release liner 48 can then be pulled (see arrow in FIG. 7) to pull the release liner 48 away from the sealing film 22, which exposes an adhesive/sealing material on its bottom surface, which allows the bottom surface of the sealing film 22 to create the second seal 26 directly to the drape 4 so as to seal off the aperture 14 in a substantially air-tight manner, thus sealing off the enclosed volume from the external atmosphere.

With reference to FIGS. 15-18, the air-tight third seal 40 is formed by an adhesive 74 arranged between the sealing liner 38 and the bottom surface of the one-piece film of the top 22 and base 20. The third seal 40 is broken by peeling the sealing liner 38 off the one-piece film, thus exposing and activating the reactor 66. When the one-piece film is sealed back against the top surface 16 of the drape 4, the reactor 66 is thus exposed to the selected gas in the enclosed volume via the aperture 14. Because the reactor 66 is now in fluid communication with the enclosed volume through the aperture 14, the reactor 66 reacts with the selected gas in the enclosed volume by consuming the selected gas.

The reactor 66 can be an oxygen scavenger, for example, as described in US 2014/0109890 A1 and/or the oxygen absorption means described in U.S. Pat. No. 8,012,169 B2, which are incorporated by reference herein. US 2014/0109890 A1 describes an air-activated heater; however, the air-activated heater described in US 2014/0109890 A1 can be used as the reactor 66 to consume oxygen within the enclosed volume, thus producing a partial vacuum/low-oxygen environment within the enclosed volume. The reactor 66 may include a reducing agent, a binding agent on a reactor substrate, or an electrolyte solution, which can be provided in an electrolyte impregnated pad. The reducing agent on the reactor substrate can be zinc, aluminum, or iron, for example.

In the subject dressing 2, the drape 4 may be flexible, and thus may collapse toward the tissue site when the selected gas is consumed by the reactor 66. In which case, the volume between the tissue site and the drape 4 may decrease proportionally as the gas is removed, thus maintaining an internal pressure in the enclosed volume that is close to the ambient air pressure in accordance with the ideal gas law (PV=nRT). Initially, $P_{atm}V_{initial}=n_{initial}RT$, or $P_{atm}V_{initial}=(n_{N2}+n_{O2})RT$. To arrive at the final condition with $P=P_{atm}$ according to $P_{atm}V_{final}=n_{N2}RT$, $V_{final}/V_{initial}$ must=$n_{N2}/(n_{N2}+n_{O2})$. In other words, if a volume beneath the drape 4 is not maintained, such as when the flexible drape 4 collapses, then negative pressure (with respect to atmospheric pressure) is not produced in the enclosed volume and instead, pressure in the enclosed volume remains equal to atmospheric pressure. However, even if the pressure beneath the drape 4 is near or equal with atmospheric pressure, a low-oxygen environment can still be achieved beneath the drape 4 since the reactor 66 is removing the selected gas from beneath the drape 4.

If the drape 4 is rigid or if the dressing 2 includes internal components that are resistant to compression, then removal of gas by the reactor 66 may not cause the drape 4 to collapse, and thus the internal pressure in the enclosed volume may decrease below atmospheric pressure. The amount of oxygen in the enclosed volume may also be reduced when using the reactor 66, thus also producing a low-oxygen environment in the enclosed volume.

The reactor 66 may include an oxygen scavenger that reacts with oxygen found in the enclosed volume. The oxygen scavenger can be zinc metal. The amount of zinc included in the cap 22 (FIGS. 1-6 and 11) or the amount of zinc included within in the enclosed volume (FIGS. 7-10) can be adjusted as desired for a particular purpose, such as for removing oxygen (i.e. the selected gas found in air) from the enclosed volume and removing any oxygen that permeates through the drape 4 for a desired period of time.

To determine the scavenger capacity needed to eliminate $O_2$ from enclosed volume and prevent a buildup of $O_2$ by permeation through the drape 4, the following variables should be determined:

size of enclosed volume ($V_{air}$) in mL;
  the permeation area ($A_P$) of the drape in $cm^2$; and
  $O_2$ permeability ($K_P$) of the drape material in mL/m²·day at 160 mmHg pressure gradient.

The permeation area ($A_P$) of the drape 4 may be the area of the drape 4 within the perimeter of the gasket 6, optionally excluding the area of the drape 4 covered by the cover assembly 18, since this uncovered portion within the perimeter of the gasket 6 is the area of the drape 4 that may allow $O_2$ to permeate into the enclosed volume through its thickness from its top surface 16 to its bottom surface 8.

The following information is assumed in order to calculate the amount of scavenger (e.g. zinc metal) needed:

Scavenging reaction: $Zn + \frac{1}{2} O_2 \rightarrow ZnO$, or 2 mol Zn/mol $O_2$;
  Atomic weight of Zn=65.38 g/mol;
  Molar volume of an Ideal Gas=22.4 mL/mmol at 0° C. and 760 mmHg pressure;
  PV=nRT, with P=pressure, V=volume, n=moles of gas, R=gas constant, T=absolute temperature; and
  $O_2$ molecules are 21% of normal air molecules.

An initial amount in mg of Zn ($Zn_{initial}$) needed for an initial elimination of $O_2$ from the enclosed volume can be calculated as follows: $V_{air}$ (mL)×(1 mmol air/22.4 mL air)×(0.21 mmol $O_2$/mmol air)×(65.38 mg Zn/½ $O_2$)=1.23 mg Zn/mL of air. In other words, to initially remove $O_2$ from the enclosed volume, and ignoring minor T and P differences from STP, the dressing needs 1.23 mg Zn per mL of air in the enclosed volume. The $Zn_{initial}$ at 760 mmHg total pressure and RH=0 and T=0° C. is thus calculated using the following formula:

$$Zn_{initial}(\text{mg}) = V_{air}(\text{mL}) \times 1.23\,\text{mg}\,Zn/\text{mL}.$$

However, over time, additional $O_2$ may permeate through the drape material into the enclosed volume. In order to eliminate this additional $O_2$ that permeates into the enclosed volume, an additional amount of Zn ($Zn_{perm}$) in mg is needed. $Zn_{perm}$ can be calculated as follows: $Zn_{perm}$ (mg)= $A_P$ ($cm^2$)×$K_P$ (mL/m²·day)×(1 m²/10⁴ $cm^2$)×(1 mmol $O_2$/22.4 mL×131 mg Zn/mmol $O_2$). In other words, ignoring minor T and P variations from STP, $Zn_{perm}$ can be calculated by using the following formula:

$$Zn_{perm}(\text{mg/day}) = 5.8 \times 10^{-4} A_P \cdot K_p.$$

For eliminating $O_2$ that permeates through the drape for a 7-day period, the amount of Zn required is calculated using the following equation:

$$Zn_{perm7day}(\text{mg}) = 4.1 \times 10^{-3} A_P \cdot K_P.$$

A total amount of Zn ($Zn_{total}$) required to consume the $O_2$ from the enclosed volume for a certain time period (in days), and assuming $P_{atm}$=760 mmHg; RH=0; T=0° C., can thus be calculated using the following equation:

$$Zn_{total}(\text{mg/day}) = (Zn_{initial}) + (Zn_{perm})$$
$$= (V_{air} \times 1.23\,\text{mg}\,Zn/\text{mL}) + (5.8 \times 10^{-4} A_P \cdot K_P).$$

The total amount of Zn ($Zn_{total}$) needed both to initially evacuate $O_2$ from the enclosed volume and to consume the additional $O_2$ that permeates through the drape for seven days can thus be calculated using the following equation:

$$Zn_{total7day}(\text{mg}) =$$
$$(Zn_{initial}) + (Zn_{perm7day}) = (V_{air} \times 1.23\,\text{mg}\,Zn/\text{mL}) + (4.1 \times 10^{-3} A_P \cdot K_P).$$

As an example, if the dressing has an enclosed volume of 25 mL, a permeable area of the drape is 100 $cm^2$, the $O_2$ permeation constant $K_P$ is 1400 mL/(m² day @160 mmHg), and assuming ambient pressure is 760 mmHg and there is zero humidity, the total zinc requirement can be calculated using the equation above for $Zn_{total7day}$ (mg) as follows:

$$
\begin{aligned}
Zn_{total7day}(\text{mg}) &= (Zn_{initial}) + (Zn_{perm}) \\
Zn_{total7day}(\text{mg}) &= (V_{air} \times 1.23\,\text{mg}\,Zn/\text{mL}) + (4.1 \times 10^{-3} A_P \cdot K_P), \\
Zn_{total7day}(\text{mg}) &= 31\,\text{mg}\,Zn + 574\,\text{mg}\,Zn \\
Zn_{total7day}(\text{mg}) &= 605\,\text{mg}\,Zn.
\end{aligned}
$$

In the present subject matter, the reactor 66 can be a substantially flat, two-dimensional reactor 66 having an area on one major surface that includes 2 g of Zn per square inch of the area of the reactor 66. Assuming the reactor 66 efficiency is only 50%, then the reactor 66 would need to have about 1200 mg Zn, which would require an area of about 0.6 $in^2$ in size, which equals 3.9 $cm^2$ (i.e., (2.54 $cm^2$/$in^2$)·0.6 $in^2$=3.9 $cm^2$). If the substantially flat, two-dimensional reactor 66 has a square shape, then the reactor 66 might be as small as 2 cm×2 cm for this 25 ml enclosed volume. If the reactor 66 were included in the cap 22, then the cap 22, assuming it is round, would have to be about 3 cm in diameter (side times square root of 2), or a little over 1 inch in diameter plus extra space to accommodate edge sealing of the reactor materials, in order to accommodate the square reactor 66. The size of the reactor 66, and thus the size of the cap 22 that accommodates such a reactor 66 (FIGS. 1-6, 11, and 15-18), may be selected based on the amount of space in the enclosed volume. The reactor 66 may have an area of 0.5-10 $cm^2$, 1-5 $cm^2$, 2-4 $cm^2$, or 3 $cm^2$. The reactor 66 may have an area less than 10 $cm^2$, less than 5, $cm^2$ less than 4 $cm^2$, or less than 3 $cm^2$. The cap 22 may have a radius R (FIG. 6) of 0.25-3 in, 0.5-2 in, 1-1.5 in, or 1 in.

The cap 22 may have a radius R less than 3 in, less than 2 inches, less than 1.5 inches, or less than 1 in.

It will be appreciated that various features of the above-disclosed embodiments and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A negative pressure dressing comprising:

a drape configured to seal to skin of a patient to define a portion of an air-tight enclosed volume under the drape and around a tissue site, the drape including an aperture extending through the drape from a top surface to a bottom surface of the drape and thus providing access to the enclosed volume under the drape;

a cover assembly selectively sealing off the aperture in an air-tight manner to prevent a bulk flow of air from an external atmosphere through the aperture and into the enclosed volume, the cover assembly including a base attached to the drape, and a top that is moveable with respect to the base between an opened position and a closed position;

a reactor configured to react with a selected gas found in air; and a sealing liner covering the reactor and forming a first seal that prevents the reactor from being exposed to the selected gas, the first seal being configured to be selectively broken so as to expose the reactor to the selected gas;

wherein the reactor is configured to be selectively put in fluid communication with the enclosed volume so as to consume the selected gas in the enclosed volume; and wherein the top, when moved to the closed position, forms a second seal that seals off the aperture in an air-tight manner to inhibit a bulk flow of air between the external atmosphere and the enclosed volume, wherein the reactor is arranged on a top surface of the top.

2. The dressing according to claim 1, wherein the first seal is broken and the reactor is put in fluid communication with the enclosed volume by moving the top to the closed position.

3. The dressing according to claim 1, wherein the top is moved to the closed position by turning the top relative to the base along a threaded joint between the top and the base.

4. The dressing according to claim 1, wherein the top is moved to the closed position by rotating the top relative to the base around a hinge.

5. The dressing according to claim 1, wherein the first seal is broken, thus exposing the reactor to the selected gas, by the sealing liner or a portion of the sealing liner being removed from the top, and wherein the exposed reactor is put in fluid communication with the enclosed volume by moving the top to the closed position.

6. The dressing according to claim 5, wherein the top is moved to the closed position by turning the top relative to the base along a threaded joint between the top and the base.

7. The dressing according to claim 5, wherein the top is moved to the closed position by rotating the top relative to the base around a hinge.

8. The dressing according to claim 5, wherein the top is moved to the closed position by snapping the top onto the base.

9. The dressing according to claim 8, wherein the top snaps onto the base by barbs on the top engaging a ridge on the base.

10. The dressing according to claim 5, wherein the top and the base together form a one-piece sealing film, and wherein the top is moved to the closed position by bending the top relative to the base along a fold in the one-piece sealing film.

11. The dressing according to claim 1, wherein the top is integrally connected to the base by a moveable joint and thereby is moveable with respect to the base between the opened position and the closed position.

12. The dressing according to claim 11, wherein the moveable joint includes a hinge joint.

13. The dressing according to claim 1, wherein the top is connectable to the base by a threaded joint, and the top can be moved between the opened position and the closed position by turning the top relative to the base.

14. The dressing according to claim 1, wherein the top is connectable to the base by a snap joint, and the top can be moved from the opened position to the closed position by snapping the top onto the base.

15. The dressing according to claim 1, wherein the top and the base together form a one-piece sealing film.

16. The dressing according to claim 1, further including an adhesive that forms an air-tight third seal between the base and the drape.

17. A negative pressure dressing comprising:

a drape configured to seal to skin of a patient to define a portion of an air-tight enclosed volume under the drape and around a tissue site, the drape including an aperture extending through the drape from a top surface to a bottom surface of the drape and thus providing access to the enclosed volume under the drape;

a cover assembly selectively sealing off the aperture in an air-tight manner to prevent a bulk flow of air from an external atmosphere through the aperture and into the enclosed volume, the cover assembly including a base attached to the drape, and a top that is moveable with respect to the base between an opened position and a closed position;

a reactor configured to react with a selected gas found in air; and a sealing liner covering the reactor and forming a first seal that prevents the reactor from being exposed to the selected gas, the first seal being configured to be selectively broken so as to expose the reactor to the selected gas;

wherein the reactor is configured to be selectively put in fluid communication with the enclosed volume so as to consume the selected gas in the enclosed volume; and wherein the top, when moved to the closed position, forms a second seal that seals off the aperture in an air-tight manner to inhibit a bulk flow of air between the external atmosphere and the enclosed volume, wherein:

the reactor is arranged in the enclosed volume;

the sealing liner covers the reactor and extends through the aperture out of the enclosed volume to an exterior of the drape; and the sealing liner is configured to be pulled through the aperture, thus breaking the first seal and exposing the reactor to the selected gas in the enclosed volume.

18. A negative pressure dressing comprising:

a drape configured to seal to skin of a patient to define a portion of an air-tight enclosed volume under the drape and around a tissue site, the drape including an aperture extending through the drape from a top surface to a bottom surface of the drape and thus providing access to the enclosed volume under the drape;

a cover assembly selectively sealing off the aperture in an air-tight manner to prevent a bulk flow of air from an external atmosphere through the aperture and into the enclosed volume, the cover assembly including a base attached to the drape, and a top that is moveable with respect to the base between an opened position and a closed position;

a reactor configured to react with a selected gas found in air; and a sealing liner covering the reactor and forming a first seal that prevents the reactor from being exposed to the selected gas, the first seal being configured to be selectively broken so as to expose the reactor to the selected gas;

wherein the reactor is configured to be selectively put in fluid communication with the enclosed volume so as to consume the selected gas in the enclosed volume; and wherein the top, when moved to the closed position, forms a second seal that seals off the aperture in an air-tight manner to inhibit a bulk flow of air between the external atmosphere and the enclosed volume, wherein:

the top and the base together form a one-piece sealing film, a release liner covers a bottom adhesive surface of the top, the release liner is selectively removeable from the bottom adhesive surface such that the bottom adhesive surface is exposed and can form the second seal against the top surface of the drape to seal off the aperture.

19. A negative pressure dressing comprising:

a drape configured to seal to skin of a patient to define a portion of an air-tight enclosed volume under the drape and around a tissue site, the drape including an aperture extending through the drape from a top surface to a bottom surface of the drape and thus providing access to the enclosed volume under the drape;

a cover assembly selectively sealing off the aperture in an air-tight manner to prevent a bulk flow of air from an external atmosphere through the aperture and into the enclosed volume, the cover assembly including a base attached to the drape, and a top that is moveable with respect to the base between an opened position and a closed position;

a reactor configured to react with a selected gas found in air; and a sealing liner covering the reactor and forming a first seal that prevents the reactor from being exposed to the selected gas, the first seal being configured to be selectively broken so as to expose the reactor to the selected gas;

wherein the reactor is configured to be selectively put in fluid communication with the enclosed volume so as to consume the selected gas in the enclosed volume; and wherein the top, when moved to the closed position, forms a second seal that seals off the aperture in an air-tight manner to inhibit a bulk flow of air between the external atmosphere and the enclosed volume, wherein:

the reactor includes zinc and the selected gas is oxygen; and the zinc is included in an amount calculated using the following formula, $$\left(V_{air} \times 1.23\,\text{mg}\,Zn/\text{mL}\right) + \left(4.1 \times 10^{-3} A_P \cdot K_P\right),$$

where $V_{air}$ is a size of the enclosed volume in mL, $A_P$ is a permeation area of the drape in $\text{cm}^2$ that allows $O_2$ to permeate into the enclosed volume through a thickness of the drape, and $K_P$ is a permeability in $\text{mL}/(\text{m}^2 \cdot \text{day})$ to $O_2$ through a thickness of the drape from the external atmosphere to a zero $O_2$ volume.

\* \* \* \* \*